United States Patent [19]

DeKerlegand

[11] 4,106,347

[45] Aug. 15, 1978

[54] ULTRASONIC INSPECTION APPARATUS FOR TUBULAR MEMBERS AND METHOD

[75] Inventor: Deke E. DeKerlegand, Lafayette, La.

[73] Assignee: W. C. Lamb, Lafayette, La.

[21] Appl. No.: 823,509

[22] Filed: Aug. 10, 1977

[51] Int. Cl.$^2$ ............................................. G01N 29/04
[52] U.S. Cl. ...................................... 73/622; 73/625; 73/634
[58] Field of Search ................ 73/618, 620, 622, 623, 73/625, 626, 634, 637, 638, 639

[56] References Cited

U.S. PATENT DOCUMENTS

| | | | |
|---|---|---|---|
| 3,327,523 | 6/1967 | Kelemencky et al. | 73/639 X |
| 4,041,773 | 8/1977 | Hauldren et al. | 73/623 X |

*Primary Examiner*—James J. Gill
*Attorney, Agent, or Firm*—Arnold, White & Durkee

[57] ABSTRACT

An ultrasonic inspection apparatus for use in inspecting drill pipe or like tubular members being tripped into or out of a well borehole comprises a plurality of ultrasonic wheel-type search units arranged on a frame which defines a vertical passage for the tubular member. The search units are symmetrically disposed around the tubular member and are urged into sonic coupling with the member by means of pneumatic cylinders each having an extendible and retractable member for radially moving its respective search unit in a horizontal plane. The search unit assembly includes a number of stabilizer guide wheels for engaging the surface of the tubular member. The pneumatic cylinder is associated with a self-relieving pressure regulator for maintaining the search wheel contact with the tubular member at a constant pressure. A method of inspecting a string of pipe during a tripping operation is also provided.

13 Claims, 4 Drawing Figures

ULTRASONIC INSPECTION APPARATUS FOR TUBULAR MEMBERS AND METHOD

CROSS-REFERENCE TO RELATED APPLICATION

This application is related to the subject matter of copending U.S. application Ser. No. 620,747 entitled "Ultrasonic Inspection Apparatus for Well Operations" filed Oct. 8, 1975, now U.S. Pat. No. 4,041,773, commonly assigned with this application and incorporated herein by reference.

BACKGROUND OF THE INVENTION

1. Field of the Invention

The invention relates to non-destructive ultrasonic testing of tubular goods for detection of small internal cracks and other types of discontinuities or imperfections. More specifically, the instant invention relates to apparatus for conducting the inspection of tubular goods employed in the drilling of oil and gas wells, while such tubular goods are being passed out of or into the well borehole during a drilling operation, to provide on-site inspection of the drill pipe employed in the drilling operation or well casing or tubing while it is being set.

2. Description of the Prior Art

The use of ultrasonic testing techniques, and specifically of ultrasonic crystals, for detecting discontinuities in metal products is a common mode of nondestructive testing. The crystals employed are typically piezoelectric crystals made of a material such as quartz. These crystals produce ultrasonic vibrations in response to a voltage or appropriate frequency impressed upon the crystal. When inspecting a tubular product for internal flaws using a reflection method, the crystal is maintained in a position relative to the surface of the product to transmit a short duration sonic wave pulse into the product at an angle such that a defect or discontinuity will cause the waves to be reflected to the crystal and produce a voltage response in the crystal. Since the crystal is de-energized immediately following the pulsed emission of a wave, reflected waves are received during de-energized periods and hence the reflected waves will produce a discernible signal which may be monitored, for example, on a cathode ray tube or a strip chart recorder. Pulse repetition rates of between 60 and 2000 pulses per second are employed for various types of inspections.

Typically, an ultrasonic inspection device will be calibrated using a standard identical to the goods being inspected. The standard may have one or more discontinuities of known magnitude so that the response of the device to known imperfections may be ascertained, and standards for accepting or rejecting the inspected goods may be established.

Ultrasonic inspection techniques are most typically employed at the site of manufacture of the articles being inspected. Thus, plate or tubular goods are typically inspected at the manufacturing plant using techniques which are well-known in the art. However, the on-site inspection of tubular goods presents different and unique problems.

In well drilling operations, drill pipe failure can be a costly and time-consuming occurrence. Washouts or drill string breakage can occur frequently if drill pipe with sufficiently serious imperfections is employed. Most frequently such failures result from internal flaws in the tubular goods being used. Confronted with such a failure, it becomes necessary to trip the pipe out of the borehole to replace the failed joint. In the case of drill string breakage, it is also necessary to fish the parted portion of the string from the borehole before drilling can be recommenced. Hence, the value of an efficacious method of inspection, particularly for internal flaws in drill pipe is obvious.

During drilling operations, the drill string is frequently tripped into and out of the borehole to replace a worn drill bit, to set casing at various levels or to conduct other operations. During these trips, it is preferred to stack the drill pipe vertically within the well derrick rather than transporting it from the elevated rig floor to racks maintained at ground level. In offshore drilling operations, it is also common to stack drill pipe vertically. Inspection of a drilling string is desirably conducted periodically, e.g., every two or three months, to detect the existence of flaws in drill pipe which would render the pipe susceptible to failure in subsequent drilling operations. Hence, to provide most efficient inspection of tubular goods in well drilling operations, it is necessary to provide an inspection device which can inspect tubular goods in a vertical portion in the well derrick. With such a device inspections could be conducted during a tripping operation made necessary by factors such as a replacement of a worn drill bit. Furthermore, since it is necessary to join individual stands of pipe (comprising typically two or three pipe joints or sections) at the rig floor level when assembling a drilling string, it is necessary that a useful inspection device be readily engaged and disengaged from about the pipe being inspected.

U.S. Pat. No. 4,020,688 discloses an effective nondestructive ultrasonic testing apparatus for inspecting tubular goods employed in the drilling of oil and gas wells as such goods are being tripped into or out of the well borehole during a drilling operation. However, this apparatus required that the transducer orientation within the wheel-like search units be readjusted for any change in the size of the tubular member being inspected. Copending U.S. application Ser. No. 620,747, discloses a similar apparatus wherein the electro-acoustic transducers are mounted on a frame by a linkage which maintains the angular relation between the transducer and the tubular member constant regardless of the size of the member being inspected. Although this apparatus overcomes the need to readjust the orientation of the transducers within the search units, it has itself produced an additional problem in that the force with which the search units are urged against the tubular members varies with the diameter of the tubular member.

Thus, there is a need for an ultrasonic testing apparatus for tubular goods which automatically readjusts the orientation of the transducers and maintains a constant force between the search units and the tubular member regardless of the diameter of the tubular member.

SUMMARY OF THE INVENTION

In accordance with the instant invention, there is provided a device for nondestructive ultrasonic inspection of tubular goods disposed in a substantially vertical position. Specifically, the instant invention provides an ultrasonic inspection apparatus which is readily movable into and out of engagement with the member being inspected while maintaining a plurality of ultrasonic search units in stable position relative to the tubular member. Accordingly, the device of this invention may be advantageously employed for inspection of tubular goods used on well operations at a well derrick while tubular members are being tripped into or out of a well borehole.

The instant invention also provides a novel method of inspecting tubular goods while they are being tripped into or out of a well borehole.

When a pipe is being tripped out of a borehole, the surface of the pipe is typically covered with drilling mud and drilling debris. Also, there may exist liquid films flowing on the interior of the pipe as the pipe is withdrawn from a liquid-filled borehole. The existence of drilling mud or debris on the exterior of the pipe can create coupling difficulties with an ultrasonic inspection device. Moreover, liquid films flowing down a pipe can create false "reflections" which would mask the existence of discontinuities or flaws which are sought to be detected. Accordingly, unless a drill pipe can be substantially cleaned during its withdrawal from the borehole, the device of the instant invention will be more typically employed to conduct the ultrasonic inspection during a pipe tripping operation into the borehole.

In accordance with a first aspect of the invention there is provided an ultrasonic inspection device wherein a plurality of ultrasonic search units mounted on a frame are maintained sonically coupled to the tubular member, and the unit is positively stabilized with respect to the tubular member while permitting relative movement of the tubular member through the inspection device. Each search unit, which includes an electro-acoustic transducer disposed at a precise angle relative to the tubular member being inspected, is mounted on the frame utilizing a fluid cylinder which maintains the angular relation between the transducer and the tubular member constant while maintaining a constant pressure between the search unit and the pipe, hence providing accurate inspection information. The cylinder eliminates adjustments which must be made in the device when pipe of different diameter is inspected.

The inspection apparatus of the invention includes a frame having a plurality of ultrasonic search units thereon, which frame may be disposed around a tubular member in the vertical position. The frame has a central vertical passage around which the search units are disposed. The passage is accessible from a direction transverse to the axis of the tubular member. Once in the vertical passage, the search units are sonically coupled with the pipe by actuation of their respective fluid cylinders. In a preferred embodiment, each search unit comprises a wheel-type unit mounted in an assembly including a plurality of stabilizer guide rollers for engaging the pipe and thereby stabilizing the unit. Hence any movement of the tubular member is absorbed by the guide rollers which then maintain the frame in position to preserve the sonic coupling of the search units through the movement.

In accordance with the novel method of this invention, tubular members suspended in a well derrick may be inspected with improved efficiency by sonically coupling a plurality of wheel-type ultrasonic search units containing electro-acoustical transducers to the member, maintaining the pipe in stable position relative to the search units, and maintaining a constant angle between each of said electro-acoustical transducers and the pipe during the inspection. As a first step, the pipe is positioned in the central passage of the inspection frame. Each search unit is urged in ultrasonic coupling with the pipe by actuating a fluid cylinder connected to the unit by a horizontally disposed cylinder rod. The pressure on each cylinder is maintained at a constant value to establish a constant pressure between the wheel and the pipe that will not vary appreciably with pipe size.

BRIEF DESCRIPTION OF THE DRAWINGS

The invention will further be illustrated by reference to the appended drawings which illustrate particular embodiments of the ultrasonic inspection apparatus in accordance with this invention.

DESCRIPTION OF THE PREFERRED EMBODIMENT

Figure 1:
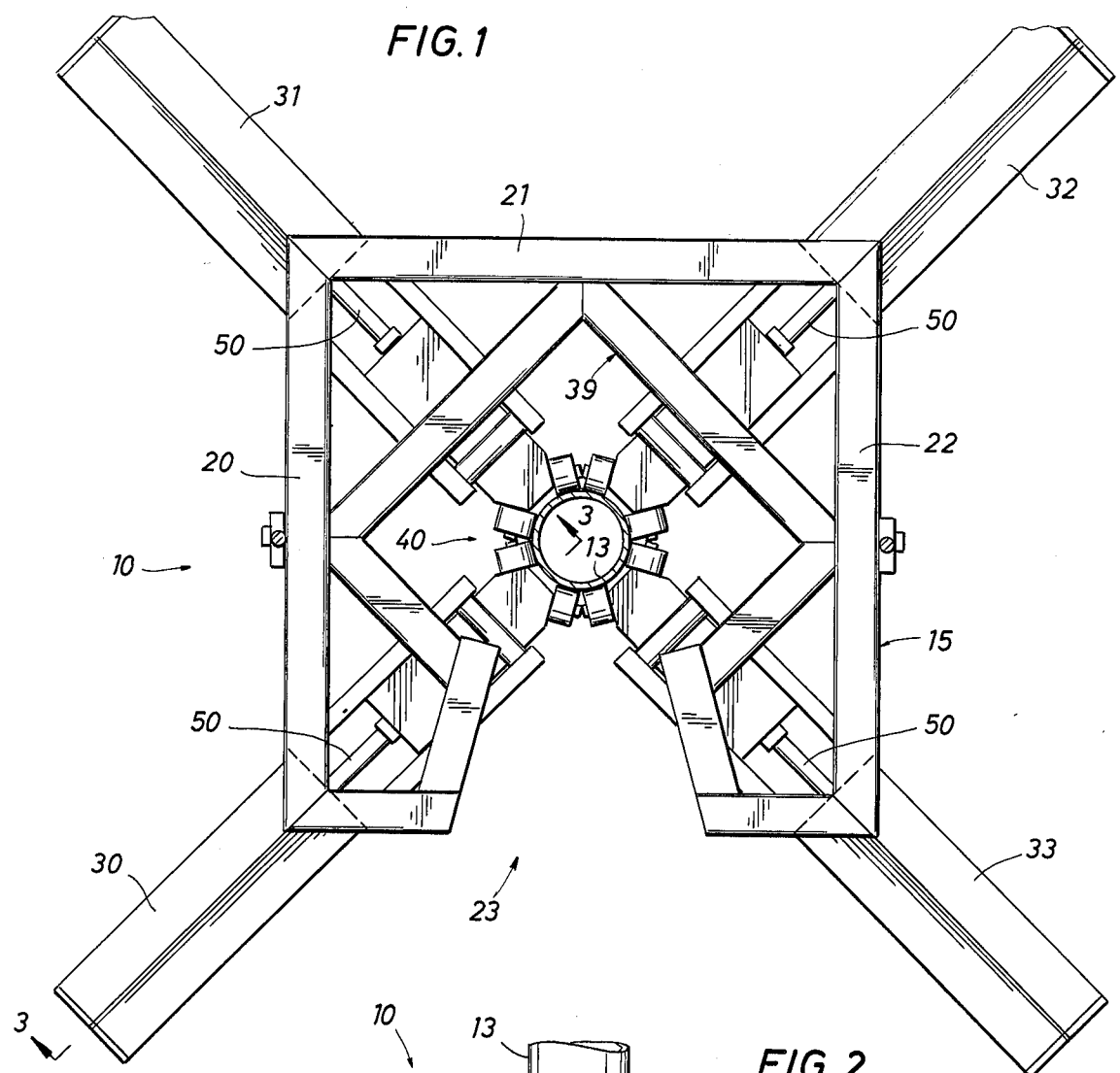
FIG. 1 is a top view of the inspection apparatus of the present invention.
Figure 2:
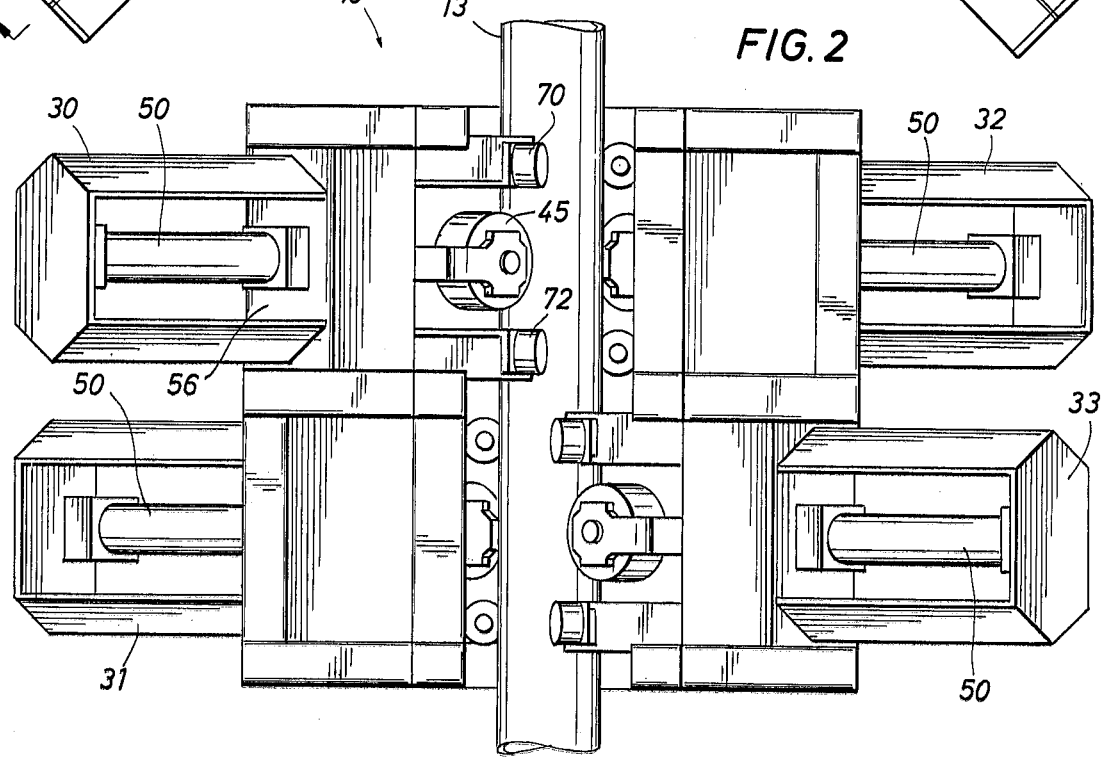
FIG. 2 is a side view of the apparatus illustrated in FIG. 1.

Referring to the drawings, in particular to FIGS. 1 and 2, there is shown an ultrasonic inspection apparatus 10 in accordance with the invention in position around a vertically disposed pipe section 13 which, for example, may be a pipe being tripped into or out of a well borehole. Apparatus 10 comprises a frame 15 which is generally square when viewed in plan as in FIG. 1. Frame 15 has three closed sides generally indicated by reference numerals 20, 21, 22 and a fourth open side 23. Frame 15 mounts four search unit assemblies 30, 31, 32, 33 which project inwardly toward pipe 13 from the corners of square frame 15. The search unit assemblies are radially symmetrically disposed about the pipe 13 with the on-line assemblies 30 and 32 positioned at a higher level than the on-line assemblies 31 and 33.

As best shown in FIG. 1, frame 15 is reinforced by truss member 39. The central portion of truss member 39 defines a central vertical passage 40 in the apparatus. As previously mentioned, frame 15 includes an open side 23 which permits the inspection apparatus to be positioned around and removed from pipe 13 quickly and easily.

Figure 3:
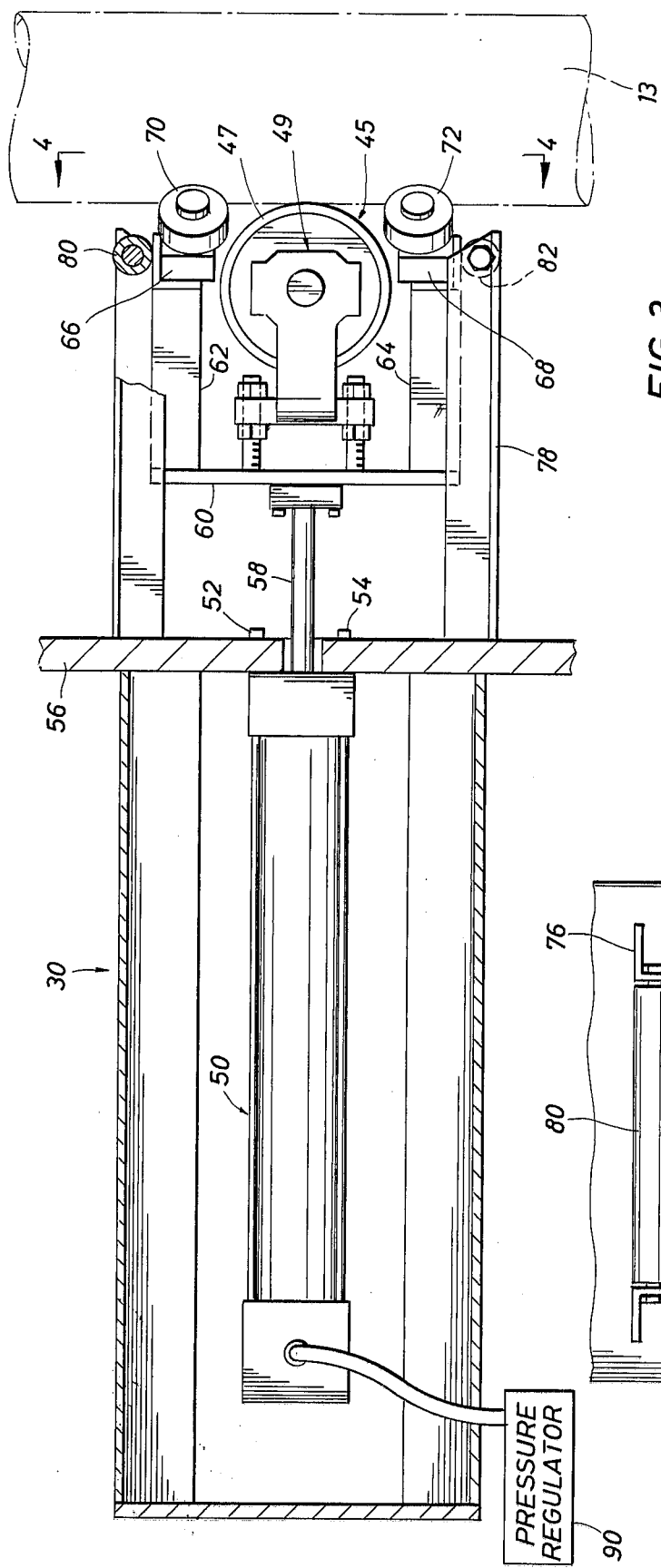
FIG. 3 is a partial section view through one of the search unit assemblies taken substantially along line 3—3 of FIG. 1.

With additional reference to FIGS. 3 and 4, the structure of a typical search unit assembly 30 will be described. Assembly 30 includes a search unit 45 having a flexible tire-like wheel 47 mounted for rotation about an axis supported by bracket 49. The piezoelectric crystal (not shown) is mounted on a non-rotating axle within the wheel 45. The flexible tire 47 is then filled with a suitable coupling agent. Coupling agents which have been used in the art include glycols or glycol ethers, for example, the Cellusolve products sold by Union Carbide Corporation. The search unit employed in the device of this invention is preferably a variable angle beam wheel search unit of a type well-known in the art. Such wheel search units are manufactured by Sperry Division of Automation Industries, Inc. A further description of a search unit of this type may be found by reference to U.S. Pat. No. 3,628,375 issued to Dominick A. Pagano.

Search unit assembly 30 further comprises a pneumatic cylinder 50 which is secured by a pair of bolts 52, 54 to a cylinder mounting plate 56. Cylinder 50 includes a retractable and extendable piston rod 58 which is secured at its outward end to an inspection wheel and guide roller mounting plate 60. Plate 60 is secured by welding or the like to a pair of upper and lower guide roller mounting channels 62 and 64. Channels 62 and 64 carry mounting blocks 66 and 68 which mount stabilizer guide rollers 70, 71, 72, 73. Channels 62 and 64 ride in a track provided by guide angles 76 and 78 and are rollably supported by transverse rollers 80 and 82.

Cylinder 50 is provided with a self-relieving pressure regulator 90 for providing a constant pressure between wheels 47, 70, 71, 72, 73 and pipe 13. Since the pressure at the wheel-pipe interface is controlled by the cylinder 50, a constant pressure can be maintained regardless of the pipe diameter. The force may, of course, be controlled by adjusting the setting of the pressure regulator.

In order to accomplish sonic coupling between the flexible tire 47 and the pipe 13 being inspected, it is preferred to provide a liquid coupling agent on the surface of the pipe. Water may be used as the coupling agent and supplied to the inspection site by the structure described in copending U.S. application Ser. No. 620,747, incorporated herein by reference.

Figure 4:
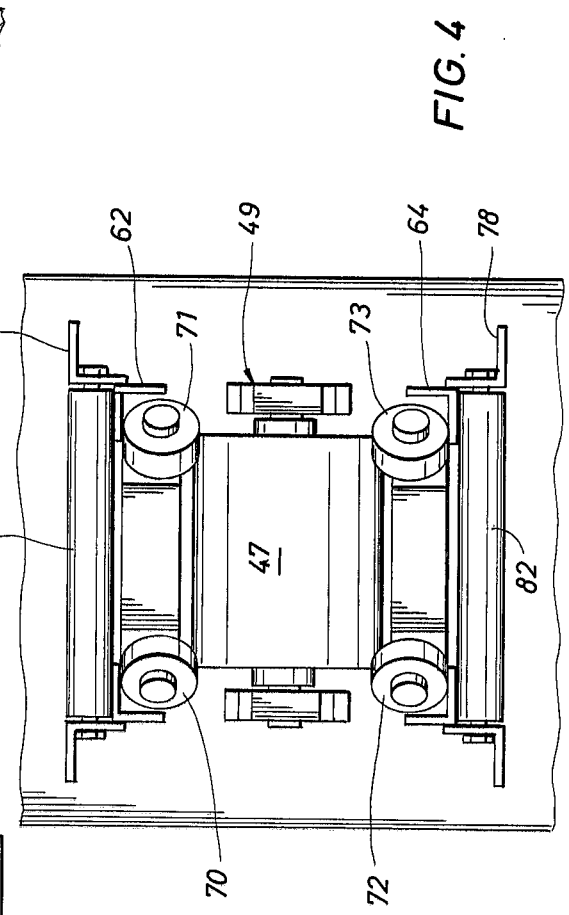
FIG. 4 is an end view of a search unit taken substantially in the direction indicated by line 4—4 in FIG. 3.

As best shown in FIG. 4, the stabilizer guide rollers 70, 71, 72, 73 have axes of rotation disposed at an angular orientation to each other to form a V-shaped opening between the surfaces of the guide rollers into which pipe 13 is received for engagement with tire 47.

It will be understood that in accordance with this invention, any desired number of ultrasonic search units may be used to effect the pipe inspection. The illustrated embodiment shows four such search units arranged around the pipe at two levels on 90° centers. However, it may be satisfactory depending on the size of the pipe, the particular inspection operation, and the beam spread of the ultrasonic transducers employed to utilize more or less ultrasonic search units. When scanning the pipe for imperfections or discontinuities transverse to the axis of the tubular member being inspected, it is sufficient so long as the beam spread permits a survey of the entire circumferance of the pipe as it passes through the apparatus. Three or four units are most often used for the transverse discontinuity inspection.

For longitudinal discontinuity inspection, the electroacoustic transducers are arranged in a plane parallel to the axis of the pipe to transmit a beam which travels around the pipe in a section generally perpendicular to the longitudinal axes. As few as two or up to four coplaner search units are used for this operation depending primarily on the diameter of the member being inspected.

Thickness measurement is effected by a sonic beam transmitted perpendicular to the surface of the pipe. This beam measures thickness only between the search units hence up to four or even more units may be employed depending upon how closely thickness is to be monitored. On a large diameter pipe, a complete thickness inspection could require more than four units. Often it may be sufficient, on the other hand, to use two search units to monitor thickness, cognizant that these units will give only a general indication of pipe condition, and are not likely to pick up all areas of wear or corrosion.

Preferably, in order to scan for discontinuities transverse to the longitudinal axis of a tubular member, the search unit should have its piezoelectric crystal disposed at an angle approximately 45° to the axis of the tubular member being inspected. This angle may vary slightly depending upon the size and thickness of the pipe being inspected. For example, on some pipe having diameters between 3½ and 4½ inches, it has been found that an attack angle of the sonic beam on the piezoelectric crystal is optimal at an angle of 43½° to the longitudinal axis of the pipe when inspecting for transverse discontinuitites. However, in determining the optimal position of the piezoelectric crystal, it is preferred to initially calibrate the unit with a standard test pipe section having a discontinuity of known dimension. The unit is activated and the angle of attack of the piezoelectric crystal is adjusted until the known discontinuity gives the maximum electrical response. Available search units have the capability of adjusting to the member being inspected and use of such variable angle beam search units is preferred.

It is desirable to be able to set up the inspection apparatus with the optimum beam angle and utilize the apparatus to inspect tubular members of various diameters without making correction adjustments to reset the beam angle. The previously desribed search unit assembly incorporating pneumatic cylinder 50 provides this desirable feature.

As described in copending U.S. application Ser. No. 620,747, an inspection apparatus may be provided with three separate tiers of search wheels with a first tier having the piezoelectric crystals oriented to detect the presence of discontinuities transverse to the longitudinal axis of the pipe, a second tier for detecting discontinuities running substantially longitudinally through the pipe and a third tier to inspect for wall thickness.

In a typical pipe inspecting operation, the cylinders 50 are first actuated to retract rods 58 to enable the pipe 13 to be received through open side 23. The device is manipulated until pipe 13 is disposed substantially centrally in the vertical passage. At this time a first pair of on-line search unit assemblies, e.g. assemblies 31 and 33, are actuated to urge their respective wheel search units into engagement with the pipe. In preferred method of practicing the invention, assembly 31 is provided with a stop rod, not shown, which may be adjusted to a selected position according to the diameter of the pipe being inspected. The cylinder for assembly 31 is first actuated so that it moves into contact with the pipe at a position determined by the adjustment of the stop rod. Then the cylinder for on-line assembly 33 is actuated so that its search unit contacts the pipe and automatically centers the pipe. Next, assemblies 30 and 32 are brought into engagement with the pipe. The passage of the stand of pipe into the borehole then commences. A typical stand of pipe includes two or more joints where the box and pin of abutting pipes are joined. A primary advantage of the invention is that when a joint is encountered, the self-relieving pressure regulation will cause assemblies 30–33 to retract thereby maintaining a constant pressure at the tire-pipe interface. If a discontinuity is detected, the cylinders 50 are actuated to retract rods 58 so that the search unit may be manually removed from pipe 13. The faulty pipe or joint may then be replaced and, after the string is reconnected, the inspection apparatus is repositioned around the pipe to continue the inspection operation.

As described in U.S. Pat. No. 4,020,688 and copending U.S. application Ser. No. 620,747, the transducers may be connected to an oscillosope or chart recorder to display the transmission from the transducers.

The foregoing description of the invention has been directed to a particular preferred embodiment for purposes of explanation and illustration. It will be apparent, however, to those skilled in the art, that many modifications and changes in both apparatus and method may be made without departing from the scope and spirit of the invention. For example, the search unit assemblies may be arranged in the same plane rather than at two levels as illustrated in FIG. 2. Also, the extendable and retractable rod may be actuated by any suitable means for maintaining a constant pressure at the interface between the tire and the pipe being inspected. For example, a hydraulic cylinder or an electrical apparatus having means for sensing the pressure and maintaining the pressure constant could be used. These and other modifications of the invention will be apparent to those skilled in the art. It is the Applicant's intention in the following claims to cover all such equivalent modifications and variations as fall within the true spirit and scope of the invention.

What is claimed is:

1. In an ultrasonic inspection apparatus of the type having a frame with a central vertical passage for receiving a substantially vertically disposed pipe, a plurality of wheel search units each operatively associated with a respective search unit assembly and adapted to be ultrasonically coupled to the pipe by urging such units into contact with the pipe in the presence of a selected coupling fluid, an improved search unit assembly for each search unit comprising:
a substantially horizontally disposed fluid cylinder longitudinally directed toward the centerline axis of the central vertical passage and having an extendable and retractable member extending therefrom;
a wheel search unit secured to said member for horizontal movement therewith into and out of ultrasonic coupling engagement with the pipe; and
means for supplying a substantially constant pressure to said fluid cylinder.

2. An apparatus as claimed in claim 1 wherein said means for supplying a substantially constant pressure comprises a self-relieving pressure regulator.

3. An apparatus as claimed in claim 1 wherein each said search unit assembly includes carriage means comprising a first carriage element mounting transverse roller means and a second carriage element engaging said roller means and supporting said search unit.

4. An apparatus as claimed in claim 3 wherein said second carriage element includes a plurality of stabilizer guide rollers for engaging the pipe.

5. An apparatus as claimed in claim 1 wherein each said search unit assembly includes first and second sets of stabilizer guide rollers mounted above and below the search unit respectively.

6. An apparatus as claimed in claim 5 wherein each said set of guide rollers comprises two rollers disposed at an angular orientation to each other to form a V-shaped opening between their surfaces into which the pipe is received.

7. An apparatus as claimed in claim 1 including four search unit assemblies adapted to be symmetrically disposed around the pipe and defining two sets of on-line assemblies arranged at different levels.

8. Apparatus for ultrasonic inspection of substantially vertically disposed tubular members which comprises:
a frame defining a vertical passage accessible from a direction transverse to the longitudinal axis of the tubular member being inspected; and
a plurality of ultrasonic search unit assemblies disposed on said frame, each of said search unit assemblies including
an ultrasonic search unit having an electro-acoustical transducer for sending an ultrasonic signal into the wall of said member,
a mount having said search unit affixed thereto,
stabilizer guide means carried on said mount above and below said search unit for engaging said tubular member to maintain said tubular member in stable relation with respect to said search unit, and
fluid pressure actuated means having an extendable and retractable member connected to said mount for radially moving said search unit in a horizontal plane between a first position wherein said search unit and said stabilizer guide means are retracted from engagement with the outer surface of said tubular member and a second position wherein said search unit and said stabilizer guide means engage the surface of the member, said fluid pressure actuated means having pressure relief means for providing self-adjustment of said search unit relative to said vertical member to enable said search unit to adapt to changes in sizes of the tubular member being inspected without substantially altering the orientation of the transducer within said search unit with respect to the surface of the tubular member and without substantially altering the pressure between the search unit and the tubular member.

9. The apparatus of claim 8 wherein said stabilizer guide means comprises:
first and second guide rollers having axes of rotation that are disposed at an angular orientation to each other to form a V-shaped opening between the surfaces of the guide rollers into which said tubular member is received,
said first and second guide rollers being mounted on a first guide roller mounting block appended to said search unit mount and extending longitudinally above said search unit; and
third and fourth guide rollers having axes of rotation that are disposed at an angular orientation to each other to form a V-shaped opening betwen the surfaces of the guide rollers into which said tubular member is received,
said third and fourth guide rollers being mounted on a second guide roller mounting block appended to said search unit mount and extending longitudinally below said search unit.

10. The apparatus of claim 8 wherein said search unit mount comprises:
a plate secured on the outward end of the extendable and retractable member of said pressure actuated means in a disposition substantially parallel to the centerline axis of said tubular member.

11. The apparatus of claim 8 wherein said fluid pressure actuated means comprises:
a pneumatic cylinder mounted in said frame to lie in a horizontal plane and to be longitudinally directed toward the centerline axis of the vertical passage; and
wherein said extendable and retractable member is a rod extending from the end of said cylinder that faces the vertical passage, said rod being movable in response to opposing unbalanced forces applied at its ends.

12. A method of ultrasonically inspecting a vertically disposed string of pipe being tripped into a well borehole comprising the steps of:
   positioning the pipe to be tested in the central vertical passage of an inspection frame assembly;
   urging a plurality of wheel search units into ultrasonic coupling with the pipe by actuating a fluid cylinder having a horizontally movable rod member connected to each wheel search unit;
   flowing a selected coupling fluid for maintaining a film between the wheel and the pipe;
   maintaiing the pressure in each such cylinder at a predetermined constant value to establish a constant pressure between the wheel and the pipe that will not vary appreciably with pipe size.

13. A method is claimed in claim 12 wherein the constant pressure is maintained by a self-relieving pressure regulator.

* * * * *